United States Patent [19]

Nakamura et al.

[11] 4,359,455

[45] Nov. 16, 1982

[54] DIAGNOSTIC TEST COMPOSITION FOR DENTAL CARIES ACTIVITY

[75] Inventors: Masakazu Nakamura; Kikuko Hamato, both of Takatsuki, Japan

[73] Assignee: Sunstar Hamigaki Kabushiki Kaisha, Takatsuki, Japan

[21] Appl. No.: 89,319

[22] Filed: Oct. 30, 1979

[51] Int. Cl.$^3$ .................... C12Q 1/00; G01N 31/22; G01N 33/48; G01N 33/52
[52] U.S. Cl. .................................. 424/7; 424/49; 435/4
[58] Field of Search .............. 424/7, 49, 9; 435/4, 435/30

[56] References Cited

U.S. PATENT DOCUMENTS

| | | | |
|---|---|---|---|
| 1,112,180 | 9/1914 | Westenfelter | 424/7 |
| 3,332,743 | 7/1967 | Green | 23/230 R |
| 3,507,269 | 4/1970 | Berry | 424/7 |
| 3,584,112 | 6/1971 | Morris | 424/7 |
| 3,746,624 | 7/1973 | Hoerman | 435/4 |
| 4,133,875 | 1/1979 | Hillman | 424/93 |

FOREIGN PATENT DOCUMENTS 54-47700  4/1979  Japan .

OTHER PUBLICATIONS

Cariostat, Shoni, Shika-Gaku Zasshi, 14, 1, 6-18, 1976.
Newbrun, Cardiology, Chapter 8, Caries Activity Tests, pp. 212-226, 1978.
Nakamura, Chem. Abs. vol. 91, 1979 Ab. No. 91:62741e.
Mercer, Dental Abs., vol. 17, Feb. 1972, pp. 79-80.
Ericsson, Dental Abs., vol. 6, Sep. 1961, p. 527.
Hardwick, Dental Abs., vol. 5, Oct. 1960, pp. 615-616.
MacGregor, J. Dent. Res., vol. 38, Oct. 1959, p. 854.
Englander, J. Dent. Res., vol. 38, Oct. 1959, pp. 848-853.
Kleinberg, Dental Abs., vol. 23, Nov. 1978, pp. 607-608.
Rosen, J. Dent. Res., vol. 44, 1965, pp. 845-849.

*Primary Examiner*—Anna P. Fagelson
*Attorney, Agent, or Firm*—Stevens, Davis, Miller & Mosher

[57] ABSTRACT

A test composition for evaluating dental caries activity, which comprise a specific amount of a saccharide (e.g. sucrose, glucose and fructose) and a pH indicator (e.g. resazurin, lacmoid, methyl red and alizarin) in water or an aqueous alcohol solution, said composition being regulated to a pH range of 6.5 to 7.0 with an alkali (e.g. sodium hydroxide) and an acid (e.g. acetic acid, tartaric acid or lactic acid). By using this test composition, a test for evaluation dental caries activity can be done within a very short period of time (e.g. about 30 minutes) by any person without requesting any specific training.

2 Claims, No Drawings

DIAGNOSTIC TEST COMPOSITION FOR DENTAL CARIES ACTIVITY

The present invention relates to a diagnostic test composition for dental caries activity, more particularly, to a composition comprising a specific amount of a saccharide and a specific pH indicator which is useful for evaluating simply, clearly the dental caries activity within a short period of time by observing change of color of the composition.

The test for dental caries activity is carried out in order to predict or determine whether the disease of dental caries will develop in the future, and hence, the test is very important from the standpoint of oral hygiene.

The test for dental caries activity is usually carried out by checking any factor which participates in the formation of dental caries. It is known that the dental caries will mainly be induced by microorganisms which are capable of producing acids in the mouth. Based on this knowledge, there have been proposed various methods for testing dental caries activity, such as a method for determining the dental caries activity by measuring the number of lactobacilli in the saliva, and a method for determining the activity by cultivating bacteria in the saliva in a medium containing a pH indicator and observing the degree of change of color of the medium with lowering of pH value (This method is well known as Snyder test). There has recently been developed as an improvement of the Snyder test, wherein the dental caries activity is evaluated by measuring selectively acids produced by an acid-producing bacteria, particularly Streptococcus mutans, which are considered to mainly participate in the occurrence of dental caries. It is also proposed to evaluate dental caries activity by using a buffer solution containing diazoresorcinol (resazurin) as an indicator (cf. U.S. Pat. No. 3,332,743). These known methods require a highly trained technique for testing bacteria, a specific reagent for giving the specificity to the composition used in the method, or a specific device or apparatus, or require an undesirably long time for the measurement (usually 24 to 72 hours). Accordingly, it is desired to find an improved method for testing dental caries activity which can be done simply within a very short period of time by any person without specific training.

As a result of the present inventors' extensive study of a test for dental caries activity based on the acid-producing capacity of bacteria in the mouth, it has been found that the evaluation of dental caries activity can easily be done within a very short period of time by any person with a specific composition which contains a saccharide as a carbon source for promoting the acid-producing capacity of bacteria in the mouth and a pH indicator which has a color change point at a pH range of 5 to 7. According to this method, a sample of dental plaque is collected and introduced into the composition, and then the change of color of the pH indicator contained in the composition is observed with the naked eye.

An object of the present invention is to provide a novel test composition useful for evaluating simply dental caries activity. Another object of the invention is to provide an improved method for testing dental caries activity within a very short period of time. These and other objects of the invention will be apparent from the following description.

The test composition for dental caries activity of the present invention comprises a specific amount of a saccharide and a specific amount of a specific pH indicator and has a pH of 6.5 to 7.0.

Since the acids produced by bacteria in the mouth are weak acids and the amount thereof is very small, the pH indicators used for the test of dental caries activity should change their color within a pH range of 3.0 to 7.0. The present inventors have experimentally found the following facts.

(1) The change of color of the pH indicator is different between when the pH value is experimentally lowered by adding an acid (e.g. lactic acid which is the main acid among the acids produced by the bacteria in the mouth) to the composition and when the pH value is lowered with acids which are produced solely by bacteria in the mouth.

(2) A carbon source is essential for promoting the acid-producing capacity of the bacteria in the mouth.

(3) No other nutrient is required for the test, and rather, if other nutrient such as yeast extract is added to the composition, the evaluation of change of color of the pH indicator is barred because of coloring of the other nutrient.

(4) Some specific pH indicators such as resazurin, lacmoid, methyl red and alizarin which have a color change point at a pH range of 5 to 7 are very sensitive to the acids produced by bacteria in the mouth and can sharply change their color within a very short period of time.

(5) When the pH indicator having a color change point within a pH range of 5 to 7 is first dissolved in an aqueous alkaline solution and the aqueous solution is adjusted to a pH of 6.7 to 7.0 with a weak acid and followed by inoculating bacteria in the mouth therein, the change of color of the indicator becomes sharper.

The above facts have been found by the following experiments.

(1) Experiment 1

To aqueous solutions of various indicators was added lactic acid to lower the pH value thereof, and the change of color of the indicator was observed. The results are shown in Table 1.

TABLE 1

| Indicators | | pH value | | | | | | | | |
|---|---|---|---|---|---|---|---|---|---|---|
| Kind | Concentration (% by weight) | 7.0 | 6.5 | 6.0 | 5.5 | 5.0 | 4.5 | 4.0 | 3.5 | 3.0 |
| Resazurin | 0.02 | Blue | Violet | Violet | Reddish Violet | Reddish Violet | Crimson | Crimson | Red | Red |
| Resazurin | 0.002 | Violet | Reddish Violet | Reddish Violet | Crimson | Crimson | Dark red | Red | Red | Red |
| Methyl Red | 0.02 | Yellow | Yellow | Bright yellow | Bright yellow | Orange | Red | Red | Red | Red |
| Alizarin | 0.002 | Red | Red | Red | Orange | Bright yellow | Yellow | Yellow | Yellow | Yellow |
| Lacmoid | 0.02 | Blue | Blue | Violet | Reddish | Crimson | Crimson | Red | Reddish | Faint |

TABLE 1-continued

| Indicators | | pH value | | | | | | | | |
|---|---|---|---|---|---|---|---|---|---|---|
| Kind | Concentration (% by weight) | 7.0 | 6.5 | 6.0 | 5.5 | 5.0 | 4.5 | 4.0 | 3.5 | 3.0 |
| | | | | | Violet | | | | orange | reddish orange |
| Lacmoid | 0.002 | Blue | Violet | Reddish violet | Crimson | Crimson | Faint red | Pink | Faint pink | Faint pink |
| BCG*1 | 0.002 | Blue | Blue | Bluish green | Bluish green | Green | Green | Yellow green | Yellow green | Yellow |
| BPB*2 | 0.02 | Blue | Blue | Blue | Blue | Blue | Violet | Violet | Reddish brown | Reddish brown |

[Remarks]:
*1Bromcresol Green,
*2Bromphenol Blue (2) Experiment 2

Various indicators were each dissolved in 0.1 N aqueous sodium hydroxide solution 10% by weight of sucrose was added, and the solution was adjusted to a fixed pH with lactic acid. The 0.002% by weight aqueous solution of indicator thus obtained (2 ml) was inoculated with a suspension of Streptococcus mutans (OMZ 176) (number of bacteria cells: $2 \times 10^9 - 4 \times 10^9$, 0.4 ml). The resulting mixture was incubated at 37° C., and the change of the pH and change of color were observed after an interval of time. The results are shown in Table 2.

the change of color was vague too. Accordingly, the pH indicator is preferably used in a concentration of 0.0001 to 0.05% by weight, more preferably 0.001 to 0.01% by weight.

(3) Experiment 3

The same suspension (0.2 ml) of Streptococcus mutans as used in the above Experiment 2 was used to inoculate a 0.002% aqueous solution of resazurin (1 ml) containing 10% by weight of the various saccharides shown in Table 3. The mixture was incubated at 37° C., and the change of color with lapse of time was observed. The results are shown in Table 3.

TABLE 2

| | Time of incubation at 37° C. | | | | | | | | | | |
|---|---|---|---|---|---|---|---|---|---|---|---|
| | Before inoculation of bacteria | | 0 minute | | 15 minutes | | 30 minutes | | 1 hour | | 24 hours | |
| Indicator | pH | Color | pH | Color | pH | Color | pH | Color | pH | Color | pH | Color |
| Resazurin | 6.8 | Blue | 6.7 | Blue | 5.9 | Reddish violet | 5.2 | Pink | 4.8 | Faint pink | 4.5 | Colorless |
| Lacmoid | 6.8 | Blue | 6.8 | Blue | 6.3 | Bluish violet | 5.2 | Faint red | 5.0 | Faint pink | 4.7 | Colorless |
| Methyl red | 6.8 | Yellow | 6.6 | Yellow | 5.6 | Bright yellow | 4.7 | Pink | 4.5 | Faint pink | 4.3 | Faint pink |
| Alizarin | 6.8 | Red | 6.7 | Red | 5.9 | Faint pink | 5.5 | Yellow | 5.0 | Yellow | 4.8 | Faint yellow |
| BCG | 6.8 | Blue | 6.8 | Blue | 6.3 | Blue | 6.0 | Blue | 5.7 | Blue | 5.5 | Bluish green |
| BPB | 6.8 | Blue | 6.8 | Blue | 6.3 | Blue | 6.1 | Blue | 5.8 | Blue | 5.1 | Bluish Violet |
| Resazurin* | 6.8 | Blue | 6.7 | Blue | 6.4 | Violet | 6.0 | Reddish violet | 5.4 | Red | 4.8 | Faint pink |

[Remark]:
*No sucrose was added.

As is clear from the results shown in Table 1 and Table 2, when the pH value of the test solution was lowered with lactic acid, all indicators showed a sharp change in color, but when Streptococcus muttans was inoculated, the specific pH indicators which change color change within a pH range of 5 to 7, such as resazurin, lacmoid, methyl red and alizarin, particularly resazurin and lacmoid, respond sharply to the acids produced by the bacteria and clearly change their color within a very short period of time. When no sucrose was added, the change of color was delayed, and hence, it is essential to add a saccharide. Moreover, when the indicator was dissolved first and thereafter the PH was adjusted with an acid, the change of color appeared more sharply.

The effect of concentration of the pH indicator was also tested. As a result, when the indicator was used in too small an amount, the change of color was vague, and on the other hand, when the amount of the indicator was too large, too much time was required for the color change and the color tone became dark. Hence

TABLE 3

| | Time of incubation at 37° C. | | |
|---|---|---|---|
| Saccharides | 0 minute | 15 minutes | 30 minutes |
| Sucrose | Blue | Red | Faint pink (transparent) |
| Glucose | Blue | Red | Dark pink |
| Fructose | Blue | Reddish violet | Dark pink |
| Starch | Blue | Reddish violet | Dark pink |

As is clear from the above results, when sucrose was used, the color of the indicator changed most rapidly, and the rate of color change was progressively lower with glucose, fructose and starch. When sucrose was used, the color change was most easily detected.

The effect of concentration of the saccharides was also tested. As a result, when the amounts of saccharides were too small, the amount of acids produced by the bacteria were too small and hence the color did not change within a short period of time, and on the other hand, when the amount of saccharides was too large, the rate of color change was too slow. Accordingly, the saccharides are preferably used in an amount of 2.5 to 40% by weight, more preferably 5 to 20% by weight.

Thus, the composition of the present invention compriese 2.5 to 40% by weight of a saccharide and 0.0001 to 0.05% by weight of a pH indicator which changes color at a pH of 5 to 7, said composition having a pH value of 6.5 to 7.0 which is adjusted with an alkali and an acid.

The composition of the invention is prepared by dissolving the fixed amount of the saccharide and pH indicator in water or an aqueous alcohol (e.g. ethanol) having a concentration of alcohol which does not produce an undesirable effect on the bacteria in the mouth, e.g. preferably about 1% by weight or lower, in water or 0.1 to 1% by weight in agueous ethanol solution, and followed by adjusting the pH thereof. In a preferred embodiment, the pH indicator is dissolved in an aqueous solution or aqueous alcohol solution of an alkali and the saccharide is thereafter dissolved and the solution is adjusted to the desired pH value with an acid.

The saccharide used in the present invention includes sucrose, glucose and fructose, among which sucrose is the most preferred. The saccharides are used in an amount of 2.5 to 40% by weight, preferably 5 to 20% by weight.

Suitable pH indicators include resazurin, lacmoid, methyl red and alizarin, among which resazurin and lacmoid, particularly resazurin, are preferred. The pH indicators are used in an amount of 0.0001 to 0.05% by weight, preferably 0.001 to 0.01% by weight, more preferably 0.001 to 0.005% by weight.

The alkalis used for adjusting the pH value of the composition include an alkali metal hydroxide (e.g. sodium hydroxide, potassium hydroxide, and lithium hydroxide), an alkaline earth metal hydroxide (e.g. magnesium hydroxide, and barium hydroxide), an alkali metal carbonate or bicarbonate (e.g. sodium carbonate, potassium carbonate, and sodium bicarbonate), among which sodium hydroxide is the most suitable. The acid used for the regulation of the pH value include lactic acid, tartaric acid, citric acid, malonic acid, oxalic acid, acetic acid, formic acid, or the like, among which lactic acid, tartaric acid and acetic acid are the most suitable. The composition is adjusted to a pH range of 6.5 to 7.0, preferably 6.7 to 7.0, with these alkalis and acids.

The composition of the present invention may optionally be mixed with an antiseptic, such as sodium azide, which does not give any undesirable effect of the growth of bacteria in the mouth. The antiseptic is used in an amount of 0.01 to 0.1% by weight, preferably 0.025 to 0.075% by weight, based on the weight of the composition.

The test for evaluating dental caries activity with the composition of the present invention is carried out by collecting a sample on dental plaque from a patient to be tested, inoculating the composition, with the dental plaque and observing the color change of the composition after incubation of the composition for a fixed period of time (e.g. 30 minutes). The change of color varies with the amount of acid produced by the bacteria, and the color changes in order of blue→reddish violet→dark pink→colorless in case of resazurin, blue→violet→red→pink in case of lacmoid, yellow→bright yellow→dark pink→pink in case of methyl red, and red→faint pink→bright yellow→yellow in case of alizarin. Since the test can be carried out within a very short period of time (e.g. 30 minutes), the test is not affected by the incubation temperature and can be carried out at a temperature of from room temperature (about 25° C.) to 37° C.

Moreover, the composition of the present invention has a selectivity to *Streptococcus mutans*, which is made clear from the following experiment.

A 0.2 ml suspension of each of the bacteria listed in Table 4 was added to a 0.002% by weight aqueous solution of resazurin (pH 6.7, 1 ml) which contained 10% by weight of sucrose the mixture was incubated at 37° C., and the change of color of the composition was observed. The results are shown in Table 4.

TABLE 4

| Bacteria | Period of incubation at 37° C. (minute) | | |
|---|---|---|---|
| | 5 | 10 | 30 |
| *Streptococcus mutans* | Reddish violet | Red | Faint pink |
| *Streptococcus sanguis* | Violet | Reddish violet | Reddish violet |
| *Streptococcus mitis* | Violet | Violet | Reddish violet |
| *Streptococcus salivarius* | Violet | Reddish violet | Red |
| *Lactobacillus casei* | Violet | Violet | Reddish violet |

As is clear from the above results, when the solution was inoculated with *Streptococcus mutans*, the color of the composition changed within a very short period of time, color change with other bacteria was slower. Thus, the composition of the present invention has a selectivity to *Streptococcus mutans*.

The preparation of the composition of the present invention is illustrated by the following Examples but is not limited thereto.

EXAMPLE 1

| Components | % by weight |
|---|---|
| Sucrose | 10 |
| Resazurin | 0.002 |
| 0.1 N aqueous sodium hydroxide solution | 5 |
| Distilled water | about 80 |
| 0.1 N lactic acid | regulated to pH 6.7-7.0 |

In accordance with the above formulation, resazurin is dissolved in a 0.1 N aqueous sodium hydroxide solution and distilled water is added thereto. Sucrose is dissolved in the solution and thereafter the composition is adjusted to pH 6.7-7.0 to provide a test composition for dental caries activity.

EXAMPLE 2

Using the same formulation as described in Example 1 except that 0.002% by weight of lacmoid is used instead of resazurin, a test composition for dental caries activity is similarly prepared.

EXAMPLE 3

Using the same formulation as described in Example 1 except that 0.02% by weight of methyl red is used instead of resazurin, a test composition for dental caries activity is similarly prepared.

Example 4

Using the same formulation as described in Example 1 except that 0.02% by weight of alizarin is used instead of resazurin, a test composition for dental caries activity is similarly prepared.

EXAMPLE 5

| Components | % by weight |
| --- | --- |
| Sucrose | 10 |
| Resazurin | 0.003 |
| 0.1 N aqueous sodium hydroxide solution | 5 |
| Antiseptic (sodium azide) | 0.05 |
| Distilled water | about 80 |
| 0.1 N lactic acid | adjusted to pH 6.7–7.0 |

In accordance with the above formulation, a test composition for dental caries activity is prepared in the same manner as described in Example 1.

What is claimed is:

1. A method for determining dental caries activity which comprises
    collecting a sample of dental plaque, mixing the collected plaque with a composition consisting essentially of 2.5 to 40% by weight of a saccharide selected from the group consisting of sucrose, glucose and fructose, 0.0001 to 0.05% by weight of a pH indicator selected from the group consisting of resazurin, lacmoid, methyl red and alizarin, and remainder of a medium selected from the group consisting of water and an aqueous alcohol solution, said composition having a pH range of 6.5 to 7, and after a predetermined period of time, observing any color change of the mixture to evaluate acid production.
2. The method of claim 1, wherein the said pH indicator is resazurin or lacmoid.

* * * * *

UNITED STATES PATENT AND TRADEMARK OFFICE
CERTIFICATE OF CORRECTION

PATENT NO. : 4,359,455

DATED : November 16, 1982

INVENTOR(S) : NAKAMURA, et al.

It is certified that error appears in the above-identified patent and that said Letters Patent is hereby corrected as shown below:

On the title page, Item [73] should read:

Assignee: from "Sunstar Hamigaki Kabushiki Kaisha" to

-- Sunstar Kabushiki Kaisha --.

Signed and Sealed this

Fifth Day of March 1985

[SEAL]

Attest:

DONALD J. QUIGG

Attesting Officer     Acting Commissioner of Patents and Trademarks